United States Patent [19]
Davis et al.

[11] Patent Number: 5,633,138
[45] Date of Patent: May 27, 1997

[54] THERMOSTABLE ALKALINE PHOSPHATASE OF THERMUS THERMOPHILUS

[75] Inventors: Maria Davis, Twinsburg; Joseph Szasz, Chesterland, both of Ohio

[73] Assignee: Amersham Life Science, Inc., Cleveland, Ohio

[21] Appl. No.: 452,988

[22] Filed: May 30, 1995

Related U.S. Application Data

[60] Division of Ser. No. 240,158, May 10, 1994, abandoned, which is a continuation-in-part of Ser. No. 229,329, Apr. 18, 1994, abandoned.

[51] Int. Cl.$^6$ .................... C12Q 1/68; C07H 21/04
[52] U.S. Cl. ........................... 435/6; 536/24.3
[58] Field of Search ............ 435/6, 183; 536/24.3

[56] References Cited

U.S. PATENT DOCUMENTS

| | | | |
|---|---|---|---|
| 4,650,760 | 3/1987 | Chlebowski et al. | 435/7 |
| 4,659,666 | 4/1987 | May et al. | 435/188 |
| 4,681,842 | 7/1987 | Rosalki | 435/21 |
| 5,248,618 | 9/1993 | Haces | 436/172 |
| 5,264,098 | 11/1993 | Chevigne | 204/182.8 |

FOREIGN PATENT DOCUMENTS

| | | | |
|---|---|---|---|
| 05236955 | 9/1993 | Japan | C12N 9/16 |
| WO9530756 | 11/1995 | WIPO | C12N 15/55 |

OTHER PUBLICATIONS

Japanese Patent Abstract 05–236955 (Sep. 17, 1993) Aoki et al., entitled: Production of Heat Resistant Alkaline Phosphatase.
Yeh and Trela (1976) J. Biol. Chem. 251:3134–9.
Hartog and Daniel (1992) Int. J. Biochem. 24:1657–60.
Smile et al. (1977) J. Biol. Chem. 252:3399–401.
Schaffel et al. (1978) Biochim. Biophys. Acta 526:457–67.
Hulett–Cowling and Campbell (1971) Biochemistry 10:1364–71.
Kam et al. (1985) Proc. Natl. Acad. Sci. USA 82:8715–19.
Sempere et al. (1986) Acta Endocrinol. 111:133–9.
Jablonski et al. (1986) Nucl. Acids Res. 14:6115–6128.
Yamamoto et al. (1992) Canadian J. Microbiol. 38:410–416.
Olive (1989) J. Clin. Microbiol. 27:261–265.
Hartog et al., "An Alkaline Phosphatase from *Thermus* sp Strain Rt41A," *Int. J. Biochem.* 24:1657–1660 (1992).
Holgrem et al., "Catalytic Properties and Stability of Three Common Variants of Placental Alkaline Phosphatase," *Medline Asseccion No. 79103184, Biochem Gent.* 16:433–442 (1978).
Huber et al., "*Metallsphaera sedula gen.* and sp. nov. Represents a New Genus of Aerobic, Metal–Mobilizing, Thermoacidophilic Archaebacteria," *System Appl. Microbiol.* 12:38–47 (1989).
Hulett–Cowling and Campbell, "Purification and Properties of an Alkaline Phosphatase of *Bacillus licheniformis*," *Biochemistry* 10:1363–1371 (1971).
Kam et al., "Cloning, Sequencing and Chromosomal Localization of Human Term Placental Alkaline Phosphatase cDNA," *Proc. Natl. Acad. Sci. USA* 82:8715–8719 (1985).
Schaffel et al., "Alkaline Phosphatase from *Bacillus licheniformis*," *Biochem. Biophys. Acta* 526:457–467 (1978).
Yeh and Trela, "Purification and Characterization of a Repressible Alkaline Phosphatase from *Thermus aquaticus*," *J. Biol. Chem.* 251:3134–3139 (1976).

*Primary Examiner*—W. Gary Jones
*Assistant Examiner*—Amy Atzel
*Attorney, Agent, or Firm*—Lyon & Lyon LLP

[57] ABSTRACT

Alkaline phosphatase from *Thermus thermophilus* has been isolated. The enzyme has a pH optimum of greater than 10.5 and is stable to heating at 65° C for 1 hour. The claimed invention relates to a method of detecting nucleic acids in a sample by providing a nucleic acid probe labelled with thermostable alkaline phosphatase from *Thermus thermophilus*; contacting the sample with said labelled nucleic acid; and detecting said nucleic acid in said sample by means of said thermostable alkaline phosphatase.

1 Claim, 6 Drawing Sheets

THERMOSTABLE ALKALINE PHOSPHATASE OF THERMUS THERMOPHILUS

This is a division of application Ser. No. 08/240,158, filed May 10, 1994, now abandoned which is a continuation-in-part of 08/229,329, filed Apr. 18, 1994, now abandoned hereby incorporated by reference in their totality (including drawings).

BACKGROUND OF THE INVENTION

Alkaline phosphatases are commonly used in routine biochemical procedures to remove phosphate groups from the terminus of a nucleic acid molecule. For example, calf intestinal alkaline phosphatase is a heat labile enzyme which is used to remove such phosphate groups, and then is inactivated by exposure to a high temperature. This thermal instability is advantageous because the alkaline phosphatase need not be removed from the reaction mixture prior to subsequent manipulations.

Alkaline phosphatase is also used as a non-radioactive marker for the detection of specific protein or DNA targets. It is conjugated to proteins or DNA oligonucleotides to aid in detection of such targets. Enzyme thermostability is desired in these applications. Alkaline phosphatases from various thermophilic and other organisms are known. Yeh et al., "Purification and Characterization of a Repressible Alkaline Phosphatase from *Thermus aquaticus*", *J. Biol. Chem.* 251:3134, 1976; Hartog et al., "An Alkaline Phosphatase from Thermus sp Strain Rt41A", *Int. J. Biochem.*, 24:1657, 1992; Schaffel et al., "Alkaline Phosphatase from *Bacillus licheniformis*", *Biochimica et Biophysica Acta*, 526:457, 1978; Hulett-Cowling and Campbell., "Purification and properties of an alkaline phosphatase of *Bacillus licheniformis*," 10 Bioc. 1364, 1971.

SUMMARY OF THE INVENTION

Applicant has isolated and purified a novel alkaline phosphatase from the thermophilic species *Thermus thermophilus*. This enzyme has an extremely high pH optimum (pH13 or greater), and is thermostable, retaining at least 50% of its activity even after 24 hours incubation at 65° C. The higher pH optimum of this enzyme is a significant advantage. This high pH optimum, and thus stability at high pH, enhances the use of the enzyme in non-radioactive detection systems, for example, when the enzyme is used with streptavidin. In addition, the high pH optimum of the enzyme makes it suitable for use with dioxetane substrates which undergo rapid conversion to the luminescent form at such alkaline pH.

The thermostability of the alkaline phosphatase is also advantageous in that following direct cross-linking of the enzyme to nucleic acid probes, it allows hybridization and subsequent washes of such labelled probes under stringent hybridization conditions, that is, at elevated temperatures without loss of enzyme activity.

Thus, in a first aspect the invention features an enzymatically active portion of the thermostable alkaline phosphatase present in *Thermus thermophilus* (Tth) having a pH optimum greater than 10.5, preferably an optimum at a pH equal to or greater than 11, which is also resistant to a temperature of at least 65° C. (i.e., maintains at least 10% of its activity at this temperature).

By "alkaline phosphatase" is simply meant a protein or fragment thereof having an activity which removes a phosphate group from a molecule, such as a DNA molecule or another molecule, such as p-nitrophenyl phosphate (pNPP). An alkaline phosphatase is one which is active at a pH greater than 7, and in the present invention has a pH optimum greater than 10.5 and preferably at pH 11 or higher. Such activity may be measured in a variety of buffers, e.g., CAPS, TRIS, TAPS, Glycine, Na phosphate and KCl-NaOH, in the presence or absence of glycerol and divalent cations. As will be shown below, the activity of the phosphatases of this invention will vary dependent on such conditions. Thus, an enzyme of this invention preferably has its activity optimum measured in the presence of glycerol in 100 mM CAPS, e.g., in the presence of calcium ions.

By "thermostable" is meant that the enzyme maintains at least 10% of its activity after heating at 65° C. for one hour or longer, preferably for 5 or 10 hours. While Applicant provides one example of an alkaline phosphatase of the present invention, those in the art armed with the fact that an alkaline phosphatase having a pH optimum of greater than or about 11 exists in nature and can be isolated can now readily screen portions of the enzyme to determine the presence of such an activity, and can use standard methodology as described herein to isolate and purify such an enzymatic portion.

In the present invention, the enzyme is preferably provided in a purified form, that is, it is isolated from the environment in which it naturally occurs. Generally, such an environment is within a bacterial cell and the protein is isolated from the cell wall and/or membranes of that cell such that it is enriched at least 10- or 100- fold compared to its presence in the cell. More preferably, it is enriched 1000- or 10,000- or more fold such that it is an essentially homogeneous preparation, that is, it is the predominant species of protein in a preparation. Even more preferably, the protein is the only species, that is, it represents at least 95% of the proteinaceous material in a sample. Such a protein may be prepared from the bacterial cells in which it naturally occurs, or may be prepared using standard recombinant DNA methodology to cause high level of expression of the protein in a bacterium or other cell in which it does not naturally occur, e.g., *E. coli*. A crude extract of such recombinant protein is included within the definition of purified protein.

Using standard techniques the enzyme described below can be readily cloned, for example, by microsequencing of the protein or fragments thereof, preparation of oligonucleotides useful as probes for a library of clones generated from the nucleic acid of a desired organism, e.g., *Thermus thermophilus*, and screening of that library with such probes to isolate fragments of DNA encoding the protein. Alternatively, an antibody to the protein may be produced and an expression library screened to determine which clone expresses an antigenic determinant recognized by that antibody. Other standard techniques are well known to those of ordinary skill in the art to isolate such genes encoding the claimed proteins. Such genes encode recombinant alkaline phosphatase.

Thus, in a second aspect the invention features recombinant alkaline phosphatase having the above properties, and cells encoding nucleic acid including such recombinant DNA. Equivalent genes encoding such phosphatases can be cloned using standard methodology.

In a third aspect, the invention features a method for use of the above enzymes in labeling of protein or nucleic acid, and in various molecular biology techniques. Thus, the enzymes of the present invention may be used in standard labeling reactions and in diagnostic assays. They may be also used in molecular biology techniques in which removal of a phosphate group is desired.

Other features and advantages of the invention will be apparent from the following description of the preferred embodiments thereof, and from the claims.

DESCRIPTION OF THE PREFERRED EMBODIMENT

The drawings will first briefly be described. Drawings FIG. 1 is a graphical representation showing the pH activity of an enzyme of the present invention;

EXAMPLE

Alkaline Phosphatase from Thermus thermophilus

Thermus thermophilus strain HB8 was grown under aerobic conditions at 75° C. in a defined media (modified from Yeh and Trela; 251 *J. Biol. Chem.* 3134, 1976) containing limiting amounts of inorganic phosphate which causes a derepression of alkaline phosphatase in this organism. The culture media contained the following salts per liter: 100 mg nitrilotriacetic acid, 60 mg $CaSO_4.2H_2O$, 100 mg $MgSO_4.7H_2O$, 8 mg NaCl, 105 mg $KNO_3$, 5 mg $ZnSO_4.7H_2O$, 5 mg $H_3BO_3$, 0.16 mg $CuSO_4.5H_2O$, 0.25 mg $Na_2MoO_4.2H_2O$, 0.4 mg $CoCl_2.6H_2O$, 22 mg $MnSO_4H_2O$, 0.28 mg $FeCl_3.6H_2O$. Vitamins were added as follows per liter: 0.1 mg biotin, 0.1 mg thiamin and 0.05 mg niacin. The media was further supplemented to 0.3% L-glutamic acid, 0.004% L-lysine, 0.1% glycerol and 0.1% glucose. Sodium glycerophosphate (40 µM) served as the source of phosphate. The pH of the media was adjusted to 7.2. Cells were harvested by continual flow centrifugation and stored frozen at −80° C.

Alkaline phosphatase activity was measured spectrophotometrically at 405 nm by following the increase in absorbance due to the release of p-nitrophenol from p-nitrophenyl phosphate (pNPP) by the enzyme at 37° C. The assay buffer contained 6 mM p-nitrophenyl phosphate, 100 mM CAPS (pH 11), and 15% glycerol unless noted otherwise.

Frozen cells were thawed, resuspended in 10 mM Tris-HCl (pH8), 1M $MgCl_2$ and 1 mM $CaCl_2$ and lysed by sonication. The lysate was cleared of cellular debris by centrifugation, dialyzed against 20 mM Tris, pH 8.0, 25 mM $MgCl_2$, 1 mM $CaCl_2$ and 0.1% Triton X 10) (buffer A) before applying to a DE52 anionic exchange column equilibrated in buffer A. The majority of alkaline phosphatase activity appeared in the flow through which was adjusted to pH 6.0 by the addition of 25 mM MES (free acid) and subsequently applied to a Heparin Sepharose CL-6B cationic exchange column. The column was developed with a linear gradient from 0 to 800 mM NaCl ($MgCl_2$ and Triton were omitted from the high salt buffer).

Fractions containing alkaline phosphatase activity (~300 mM NaCl) were pooled and applied directly to a hydroxylapatite column which was washed extensively with 20 mM Tris pH 7.4 and then developed with a linear gradient from 20 to 500 mM Na Phosphate pH 7.0. The majority of alkaline phosphatase activity eluted at ~100 mM Na Phosphate.

Preliminary analysis of the preparation by SDS-PAGE suggested that the peak of enzyme activity corresponded to a major protein band which migrated at an apparent molecular weight of ~49,000 daltons. Further purification and analysis is required to confirm this assignment. The final product was ~80% homogeneous for the 49 kd polypeptide and represented an ~10-fold purification from the crude extract as determined by specific activity studies.

Figure 1:
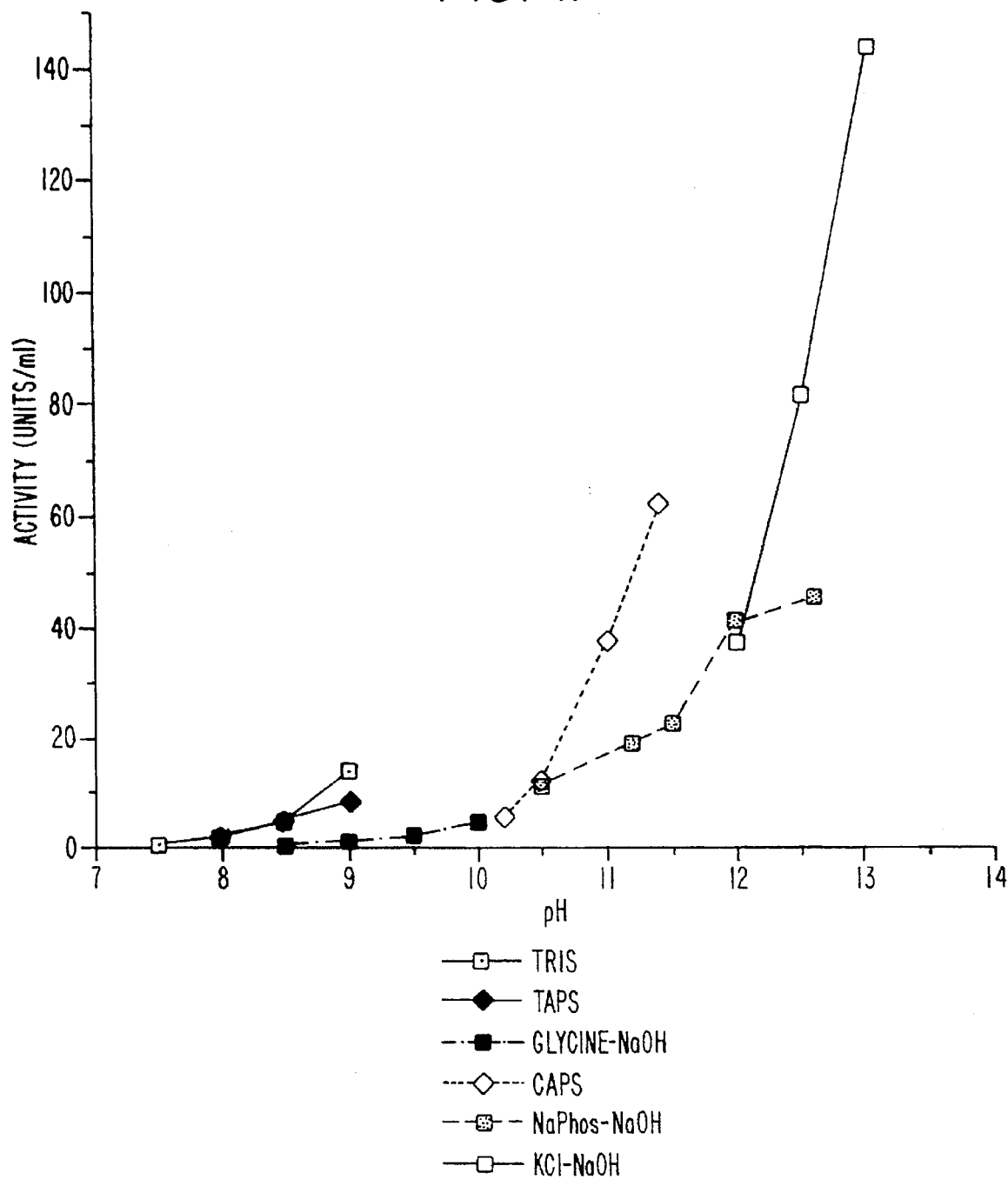
Figure 2:
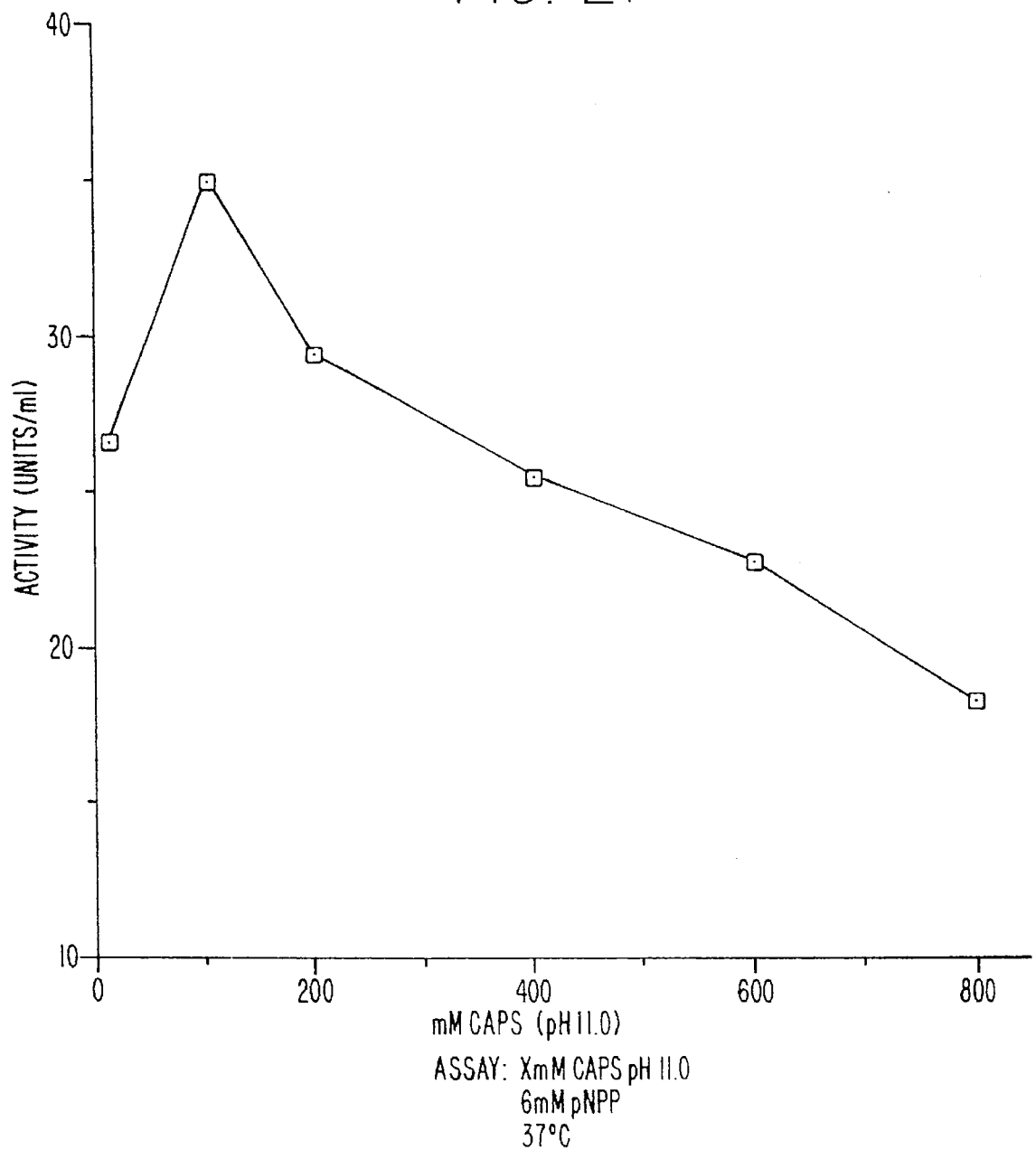
FIG. 2 is a graphical representation showing the activity (optimum) of an enzyme of the present invention in various concentrations of CAPS buffer at pH 11.0.
Figure 3:
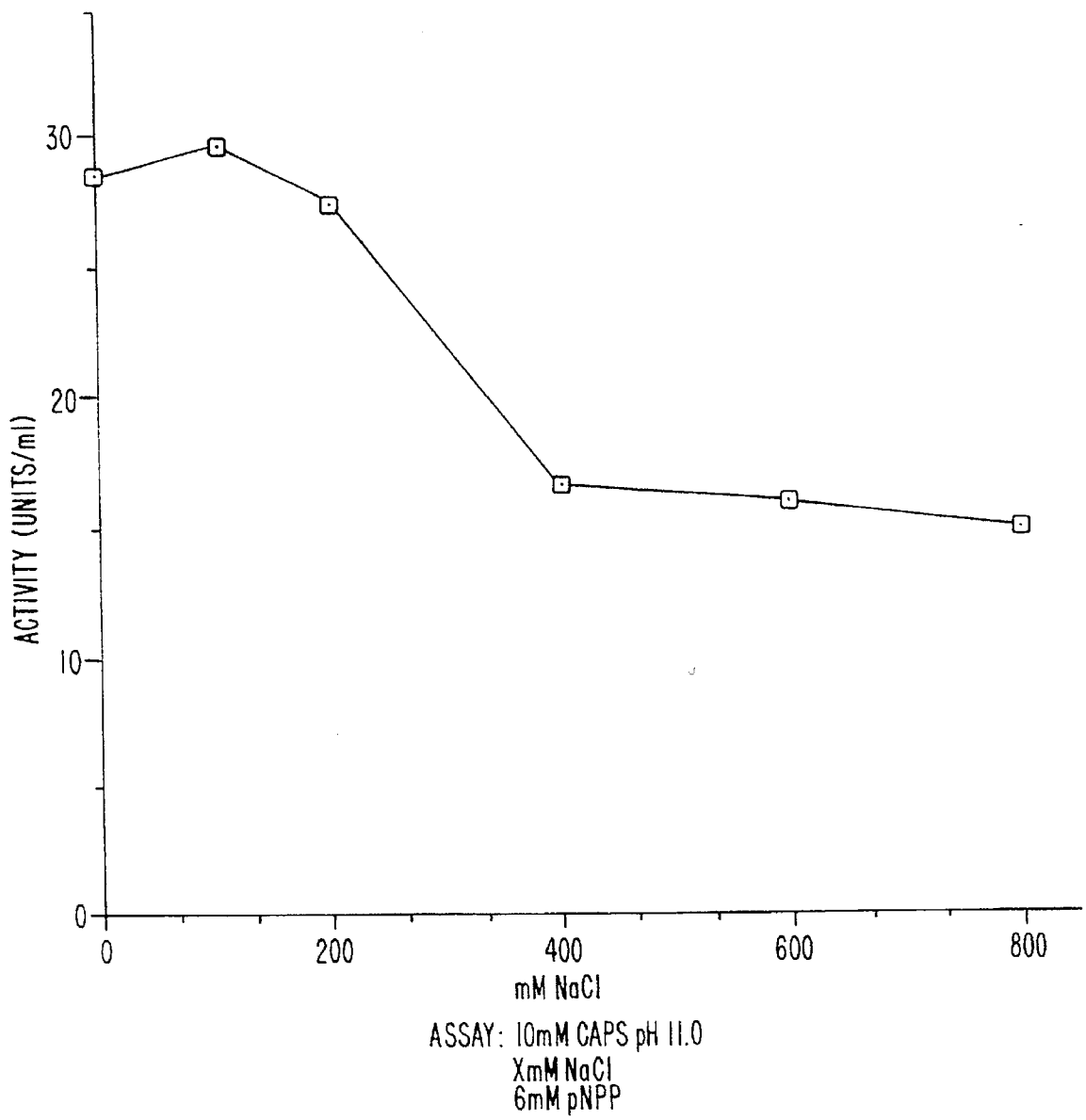
FIG. 3 is a graphical representation showing the activity (optimum) of an enzyme of the present invention in various concentrations of NaCl.
Figure 4:
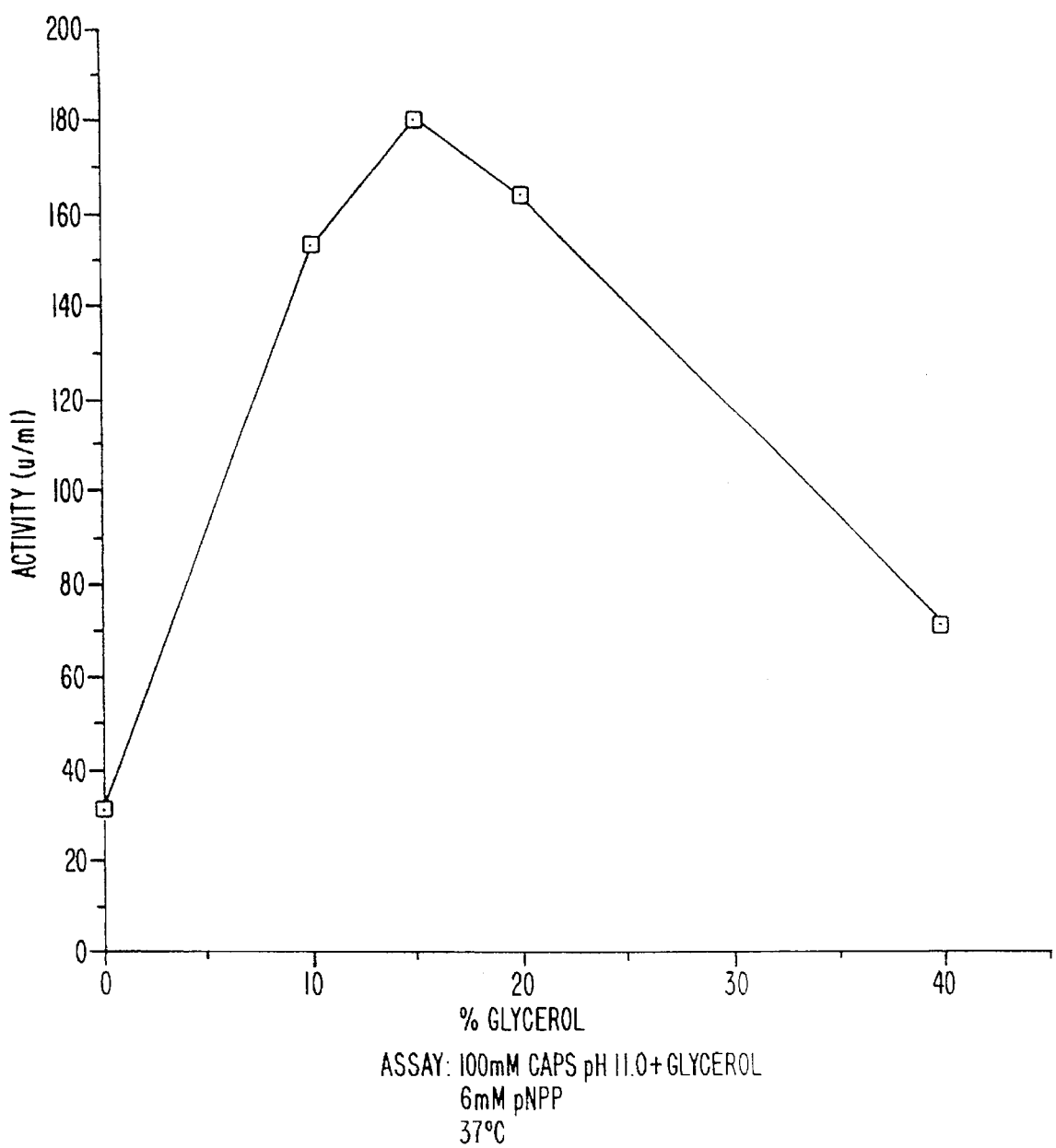
FIG. 4 is a graphical representation showing the activity (optimum) of an enzyme of the present invention in various concentrations of glycerol.
Figure 5:
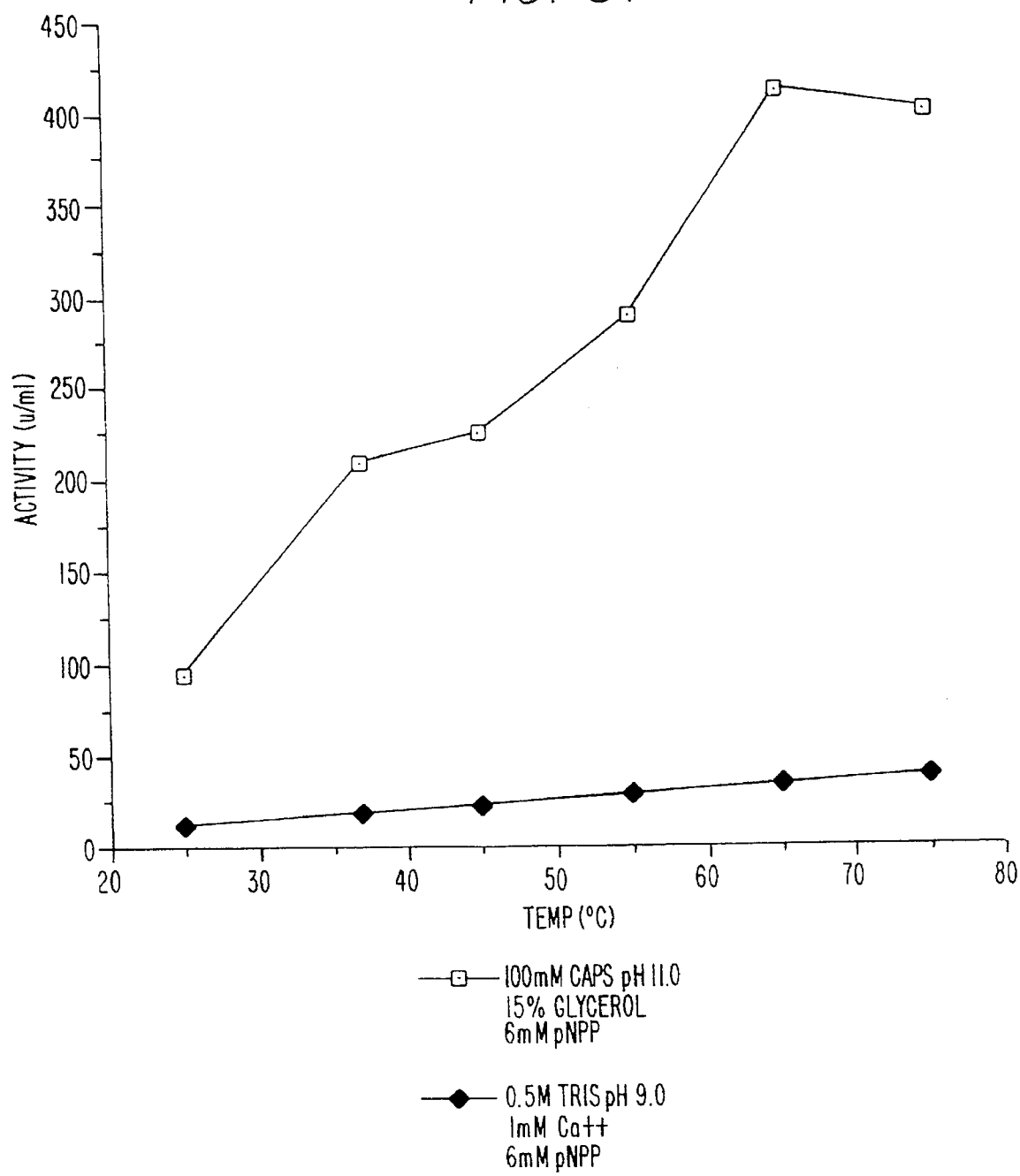
FIG. 5 is a graph showing the activity (optimum) of an enzyme of the present invention at various temperatures.
Figure 6:
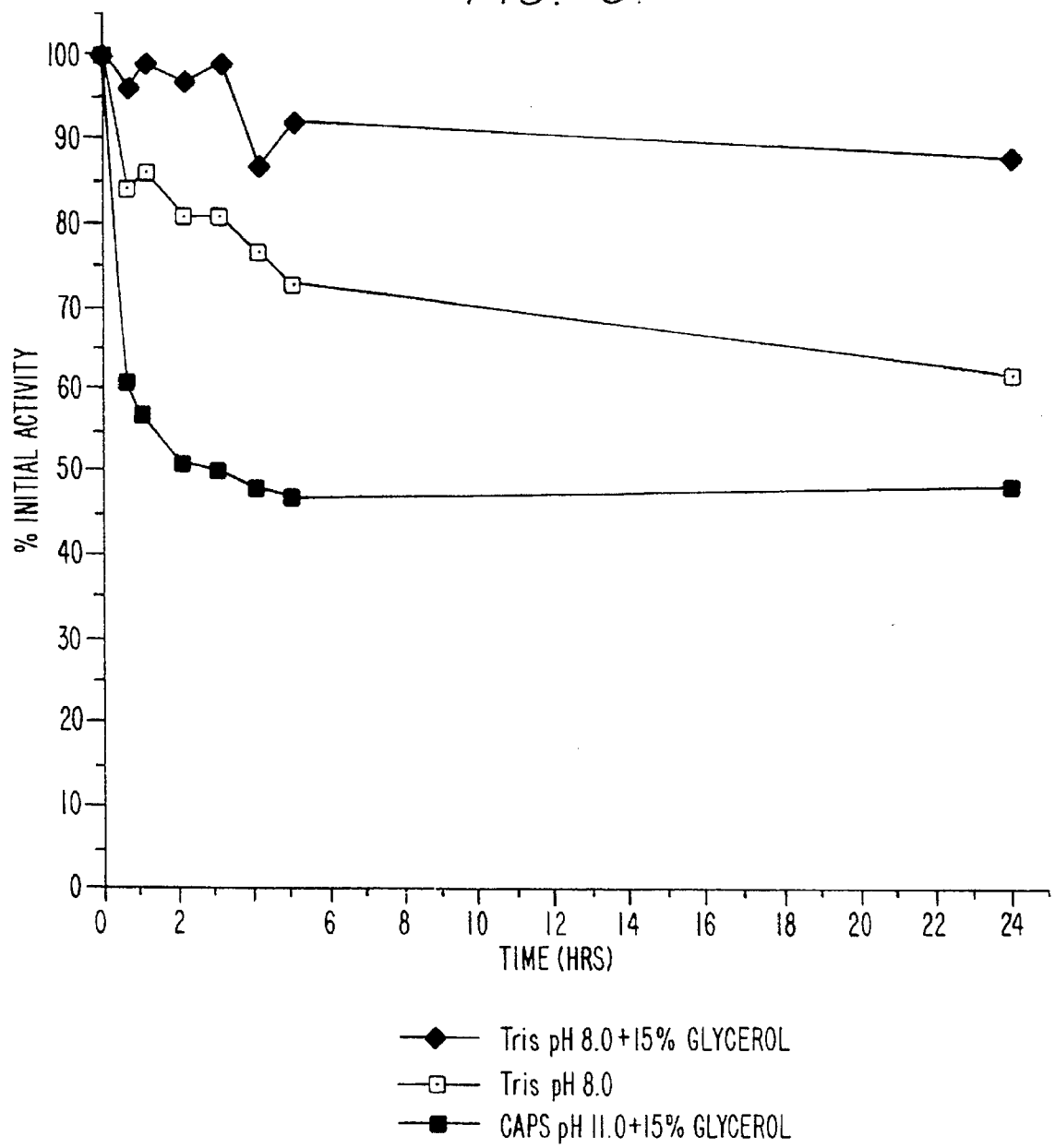
FIG. 6 is a graph showing the stability of the enzyme after heating at 70° C. for up to twenty four hours in various buffers.

Tth alkaline phosphatase displays measurable activity over a rather broad range of pH values, but appears to have an unusually high pH optimum, with 13.0 being the highest assayed (FIG. 1). Since application at such an extreme pH are infrequent, most of the characterizations were carried out at pH 11.0. Under optimized conditions (100 mM CAPS pH 11.0, 15% glycerol) the enzyme displays a specific activity of $\geq 250$ units per mg at 37° C. Enzyme activity is affected by a variety of other factors, including buffer (FIGS. 1 and 5), ionic strength (FIGS. 2 and 3), glycerol (FIG. 4) and temperature (FIG. 5). The enzyme also appears to have a requirement for divalent cation as it is inhibited by 1 mM EDTA (data not shown). However, the addition of $Ca^{++}$, $Mg^{++}$, $Mn^{++}$, $Co^{++}$, $Cu^{++}$, or $Zn^{++}$ to the assay mixture either failed to stimulate activity or was found to be inhibitory. More routine experiments can readily determine metal ion requirements of this enzyme. The protein appears to be quite thermostable as it retains nearly 90% of its activity after 24 hours incubation at 70° C. (FIG. 6). While more active in CAPS buffer, the enzyme appears to be more stable in Tris. It is unclear whether the activity in Tris is due to a pH effect or a buffer effect, but the enzyme activity is stimulated by high concentrations of this buffer.

Uses

*Thermus thermophilus* alkaline phosphatase may be a potentially useful enzyme for the non-isotopic detection of proteins and nucleic acids. For example, the thermostability of this enzyme may make it a good candidate for direct crosslinking to DNA probes which could then be hybridized to specific targets under stringent conditions (i.e., elevated temperatures). In addition, the broad temperature activity range of this enzyme (FIG. 5), permits flexibility in choice of assay temperature. Finally, the extremely high pH optimum of Tth alkaline phosphatase may make it uniquely suitable for applications at high pH.

Specifically, the alkaline phosphatases of this invention have several potential uses in the numerous non-isotopic methods for the detection of proteins and nucleic acids. For example, the high pH optimum of this enzyme makes it suitable with dioxetane substrates which undergo rapid conversion to the luminescent form at alkaline pH. In addition, the high thermostability of this alkaline phosphatase makes it useful for direct crosslinking to nucleic acid probes. Hybridization and subsequent washes can be carried out under stringent conditions (i.e., elevated temperatures) without loss of enzyme activity. When using streptavidin conjugated alkaline phosphatase on positively charged membranes, as in nucleic acid hybridization, pH greater than 9.5 is preferred to give decreased background.

Alkaline phosphatases from different organisms may (or may not) behave similarly during purification. The high pH optimum for activity cannot be exploited for the purification per se, but see below for screening. The high temperature optimum will be useful in purifying such enzymes after cloning into hosts that grow at a moderate temperature, such as *E. coli*. Extracts from *E. coli* could be heat treated to precipitate all proteins that denature at elevated temperatures.

If an enzyme is desired which is stable at 65°–75° C., it is possible to enhance the chances of discovery of such an enzyme by trying to isolate novel organisms that grow well at those temperatures. One could also select for organisms that are tolerant of high pH. In addition, knowing that an alkaline phosphatase is desired, one can then screen organisms, or libraries of recombinant clones, for alkaline phosphatase activity by use of the compound 5-bromo-4-chloro-3-indolyl phosphate (X-Phos). A blue color is obtained when the phosphate group is removed from this compound, making it very convenient to screen for activity. A pH activity profile would then be prepared to determine whether the phosphate removing activity was an alkaline phosphatase, Other embodiments are within the following claims.

We claim:

1. Method for detecting nucleic acid in a sample comprising the step of providing a nucleic acid probe labelled with a thermostable alkaline phosphatase isolated from *Thermus thermophilus*; contacting the sample with said labelled nucleic acid; and detecting said nucleic acid in said sample by means of said thermostable alkaline phosphatase.

\* \* \* \* \*